(12) United States Patent
Meoni (10) Patent No.: US 10,829,306 B2
(45) Date of Patent: Nov. 10, 2020

(54) TRANSPORT GROUP FOR CONTAINER STERILIZATION APPARATUSES

(71) Applicant: I.M.A. INDUSTRIA MACCHINE AUTOMATICHE S.P.A IN SIGLA IMA S.P.A., Ozzano Dell'Emilia (IT)

(72) Inventor: Eddi Meoni, Ozzano Dell'Emilia (IT)

(73) Assignee: I.M.A. INDUSTRIA MACCHINE AUTOMATICHE S.P.A IN SIGLA IMA S.P.A., Ozzano Dell'Emilia (IT)

( * ) Notice: Subject to any disclaimer, the term of this patent is extended or adjusted under 35 U.S.C. 154(b) by 261 days.

(21) Appl. No.: 16/082,061

(22) PCT Filed: Mar. 2, 2017

(86) PCT No.: PCT/EP2017/054943
§ 371 (c)(1),
(2) Date: Sep. 4, 2018

(87) PCT Pub. No.: WO2017/149088
PCT Pub. Date: Sep. 8, 2017

(65) Prior Publication Data
US 2020/0290811 A1    Sep. 17, 2020

(30) Foreign Application Priority Data
Mar. 3, 2016  (IT) .................. 102016000022285

(51) Int. Cl.
*B65G 17/46*   (2006.01)
*A61L 2/20*    (2006.01)
(Continued)

(52) U.S. Cl.
CPC .............. *B65G 17/46* (2013.01); *A61L 2/208* (2013.01); *A61L 2/26* (2013.01); *B65G 17/06* (2013.01);
(Continued)

(58) Field of Classification Search
CPC ...... B65G 17/32; B65G 17/42; B65G 17/065; B65G 17/46; B65G 17/063; B65G 17/067;
(Continued)

(56) References Cited

U.S. PATENT DOCUMENTS 1,737,819 A * 12/1929 Wetmore .............. C03B 35/062
198/803.14
2,522,912 A *  9/1950 Weiss ..................... B08B 9/423
198/867.08
(Continued)

FOREIGN PATENT DOCUMENTS

AU     2002354394 A1   6/2003
DE        3701079 A1   7/1988
(Continued)

OTHER PUBLICATIONS

International Search Report dated May 17, 2017 re: Application No. PCT/EP2017/054943, pp. 1-4, citing: WO 03/051759 A1, FR 2 857 350 A1, JP S54 127377 U, DE 37 01 079 A1, WO 2011/072628 A1, U.S. Pat. No. 5,337,886 A and JP 2012 200376 A.
(Continued)

*Primary Examiner* — James R Bidwell
(74) *Attorney, Agent, or Firm* — Cantor Colburn LLP (57) ABSTRACT

A transport group for container sterilization apparatuses a includes a conveyor belt, which defines an operational plane and advances along an advancement direction, and a number of support elements, mutually separated, and integral and movable with the conveyor belt. Each support element has longitudinal development transverse to the advancement direction and lying along a direction parallel to the operational plane. Each support element defines a number of
(Continued)

shaped seats arranged along the longitudinal development. Each shaped seat is adapted to temporarily house a respective container.

11 Claims, 6 Drawing Sheets

(51) Int. Cl.
  *A61L 2/26* (2006.01)
  *B65G 17/06* (2006.01)
(52) U.S. Cl.
  CPC ... *A61L 2202/23* (2013.01); *B65G 2201/0235* (2013.01); *B65G 2207/26* (2013.01)
(58) Field of Classification Search
  CPC ........ B65G 2201/0244; B65G 2207/26; B65B 55/02; B65B 55/04; A61L 2/26; A61L 2202/23; A61L 2/07; A61L 2/20; B67C 7/0073; B67B 3/24
  USPC .......................... 198/867.11, 803.14, 803.15
  See application file for complete search history.

(56) References Cited

U.S. PATENT DOCUMENTS

| | | | | |
|---|---|---|---|---|
| 3,150,765 | A * | 9/1964 | Ellis | B65G 17/063 198/867.14 |
| 3,815,758 | A * | 6/1974 | Vandergeeten | B08B 9/423 211/74 |
| 3,915,293 | A * | 10/1975 | Melchiorre | B07C 3/082 198/408 |
| 5,287,957 | A * | 2/1994 | Iuchi | B65B 43/54 198/803.14 |
| 5,325,974 | A * | 7/1994 | Staehs | A47F 7/0021 198/867.01 |
| 5,337,886 | A | 8/1994 | Anderson et al. | |
| 5,840,261 | A * | 11/1998 | Monch | A61L 2/26 422/300 |
| 6,141,939 | A * | 11/2000 | Pedrotti | B65B 7/2814 53/314 |
| 7,918,334 | B2 * | 4/2011 | Gaetano | A23G 3/2046 198/867.12 |
| 8,220,616 | B2 * | 7/2012 | Manders | B65G 47/1471 198/459.5 |
| 2014/0027651 | A1 * | 1/2014 | Kawasaki | B65G 47/84 250/453.11 |

FOREIGN PATENT DOCUMENTS

| | | |
|---|---|---|
| DE | 03051759 A1 | 6/2003 |
| FR | 2857350 A1 | 1/2005 |
| JP | S54127377 U | 9/1979 |
| JP | 2012200376 A | 10/2012 |
| WO | 2011072628 A1 | 6/2011 |

OTHER PUBLICATIONS

Written Opinion dated May 17, 2017 re: Application No. PCT/EP2017/054943, pp. 1-4, citing: WO 03/051759 A1 and FR 2 857 350 A1.

* cited by examiner

TRANSPORT GROUP FOR CONTAINER STERILIZATION APPARATUSES

TECHNICAL FIELD

The present disclosure relates to a transport group for container sterilization apparatuses.

BACKGROUND

Conventional sterilization apparatuses generally comprise a feed station (through which the containers are introduced on an internal conveyor), a sterilization station (which corresponds to a superheating of an internal chamber in which the containers are located), and a cooling station (which is necessary in order to reduce the temperature of the containers within a range that does not damage the products that said containers are designed to contain).

The containers can be bottles, test tubes, vials, syringes, carpules, jars and the like, and therefore can have different shapes and dimensions: the sterilization apparatus must be able to convey them all, i.e., it must be versatile enough to process all the types of container in all the corresponding possible sizes.

Internal conveyors are currently of the format-dependent type, i.e., must be replaced when the shape and size of the container to be sterilized changes.

If the conveyor is not changed when the shape and size of the container changes, problems in the stability of the container can arise and, in the case of conveyors suitable to transport the bulkiest containers, these conveyors are scarcely utilized if it is necessary to convey small containers. A partition is in fact provided on the conveyor between each container and the adjacent one and corresponds to the size of the bulkiest container, with the consequence of having many empty spaces on said conveyor during the conveyance of small containers.

Any constructive solutions that allow to utilize in the best possible manner the conveyance surface of the conveyor entail complex operations for changing format when passing from one type of container to another: it is therefore observed that in any case even these constructive architectures are not versatile and simple to utilize.

SUMMARY

The aim of the present disclosure is to solve the problems described above, by proposing a transport group for container sterilization apparatuses that is suitable to convey containers having substantially any shape and size.

Within this aim, the disclosure proposes a transport group for container sterilization apparatuses that allows to maximize the number of containers conveyed simultaneously as a function of their dimensions.

The disclosure also proposes a transport group for container sterilization apparatuses that does not require complex operations for changing format.

The disclosure further proposes a transport group for container sterilization apparatuses that is easy to use.

The present disclosure provides a transport group for container sterilization apparatuses that has relatively modest costs, is relatively simple to provide in practice and is safe in application.

This aim and these and other advantages which will become better apparent hereinafter are achieved by providing a transport group for container sterilization apparatuses according to claim 1.

Preferred embodiments of the disclosure are defined in the dependent claims.

BRIEF DESCRIPTION OF THE DRAWINGS

Further characteristics and advantages of the disclosure will become better apparent from the description of some preferred but not exclusive embodiments of the transport group for container sterilization apparatuses according to the disclosure, illustrated by way of nonlimiting example in the accompanying drawings, wherein.

DETAILED DESCRIPTION OF THE DRAWINGS

With reference to FIGS. 1-7, a transport group 1 for apparatuses for sterilizing containers A comprises a conveyor belt 2, which forms an operational plane and advances along an advancement direction, and a plurality of support elements 3, which are mutually separated and each of which comprises a plurality of shaped seats 4 for housing temporarily respective containers A.

Each support element 3 is integral with the respective portion of the conveyor belt 2 on the operational plane and is separated by adjacent support elements 3.

The support elements 3 advance integrally with the conveyor belt 2 along the advancement direction.

The support elements 3 have a transverse longitudinal development that is advantageously perpendicular with respect to the advancement direction and lies on a plane that is parallel to the operational plane of the conveyor belt 2. The shaped seats 4 are arranged on the support element 3 along a direction that is parallel to said longitudinal extension.

Advantageously, the shaped seats 4 have a substantially V-shaped cross-section, such as to be able to accommodate containers of different size within a predetermined range.

Advantageously, the shaped seats 4 further have a longitudinal extension that is inclined with respect to the advancement direction, so that the containers A are inclined with respect to said advancement direction when they are moved by the conveyor belt 2.

Advantageously, the shaped seats 4 have a longitudinal extension that is inclined with respect to the advancement direction and lies on a plane that is perpendicular to the operational plane and is parallel to the advancement direction.

The containers A make contact with the respective shaped seats 4 in at least two points, advantageously along two lines.

According to a particular constructive solution of unquestionable interest in practice and in application, shown in FIGS. 1 to 5, each support element 3 can validly comprise a base laminar element 5, which is integral with the conveyor belt 2, and a shaped plate 6 that is integral with the base laminar element 5. Advantageously, the shaped plate 6 protrudes and is substantially inclined with respect to the base laminar element 5. The shaped plate 6 can advantageously be made of metal plate (or other material suitable to provide sheets and plates of low thickness).

Advantageously, at least one portion of the shaped plate 6 can validly be provided with through holes 6*a* and/or with through slots in order to reduce heat inertia.

Advantageously, the shaped plate 6 comprises a series of concave portions which are alternated with a corresponding series of convex portions, which form a series of contiguous recesses arranged along a direction that is transverse, advantageously perpendicular, with respect to the advancement direction of the conveyor belt 2 and is parallel to the operational plane. In other words, the shaped plate 6 comprises a series of contiguous folds which form respective recesses. Substantially, the shaped plate 6 comprises a succession of consecutive tracts which are mutually inclined so as to form a continuous succession of concavities, which constitutes the shaped seats 4, and convexities.

This configuration is very simple to provide, even by using stainless steel or other alloys suitable to tolerate being subjected to onerous thermal cycles (continuous entry and exit in and from the sterilization chamber) and being subjected to aggressive atmospheres (for example the presence of hydrogen peroxide vapors).

The possibility to provide the support elements 3 using a nonmetallic element material, such as for example a polymeric material and/or a composite material, is not excluded.

Each recess can constitute the shaped seat 4. Each shaped seat 4 is suitable to accommodate temporarily a respective container A.

Each recess is formed between two converging planar portions of the shaped plate 6, which have a substantially V-shaped cross-section, such as to be able to accommodate containers of different size within a predetermined range.

This constructive solution is particularly interesting since it allows to convey easily containers A having the most disparate shapes and dimensions. In particular, the containers are inclined with respect to a vertical direction and are supported in a lower region and laterally by the support element 3.

In the case of relatively small containers A, they are distributed so as to occupy each shaped seat 4 of the shaped plate 6; containers A of relatively large size are distributed so as to leave a predefined number of empty seats 4 between adjacent containers A.

It is deemed useful to point out that between the base laminar element 5 and the shaped plate 6 there are interposed support ribs 7 which are substantially perpendicular to the base laminar element 5.

These support ribs 7 ensure that no flexing of the shaped plate 6 occurs when a large number of containers A is loaded onto it.

The support elements 3 further comprise a lower ledge 8, which is advantageously perpendicular to the shaped plate 6.

Each container A is housed in a respective shaped seat 4, resting in a lower region on the ledge 8 with one of its bases and resting laterally against the shaped seat 4 with at least one of its lateral portions.

Advantageously, each support element 3 is coupled to at least one driving element 9, of the type preferably selected from a chain, a belt, a cable and the like, operatively associated with a drive unit.

Figure 1:
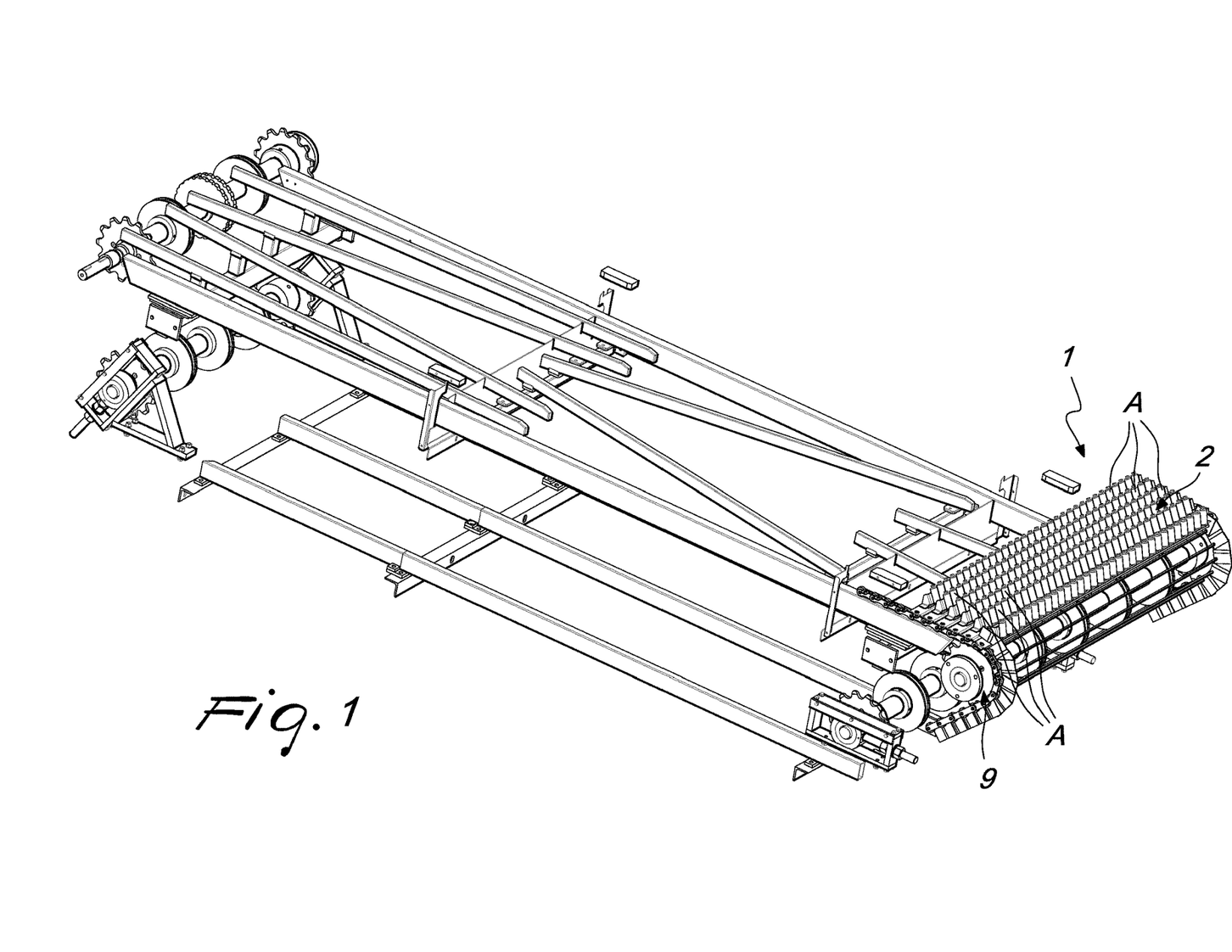
FIG. 1 is a perspective view of a transport group for container sterilization apparatuses according to the disclosure, with some parts removed for the sake of clarity.
Figure 2:
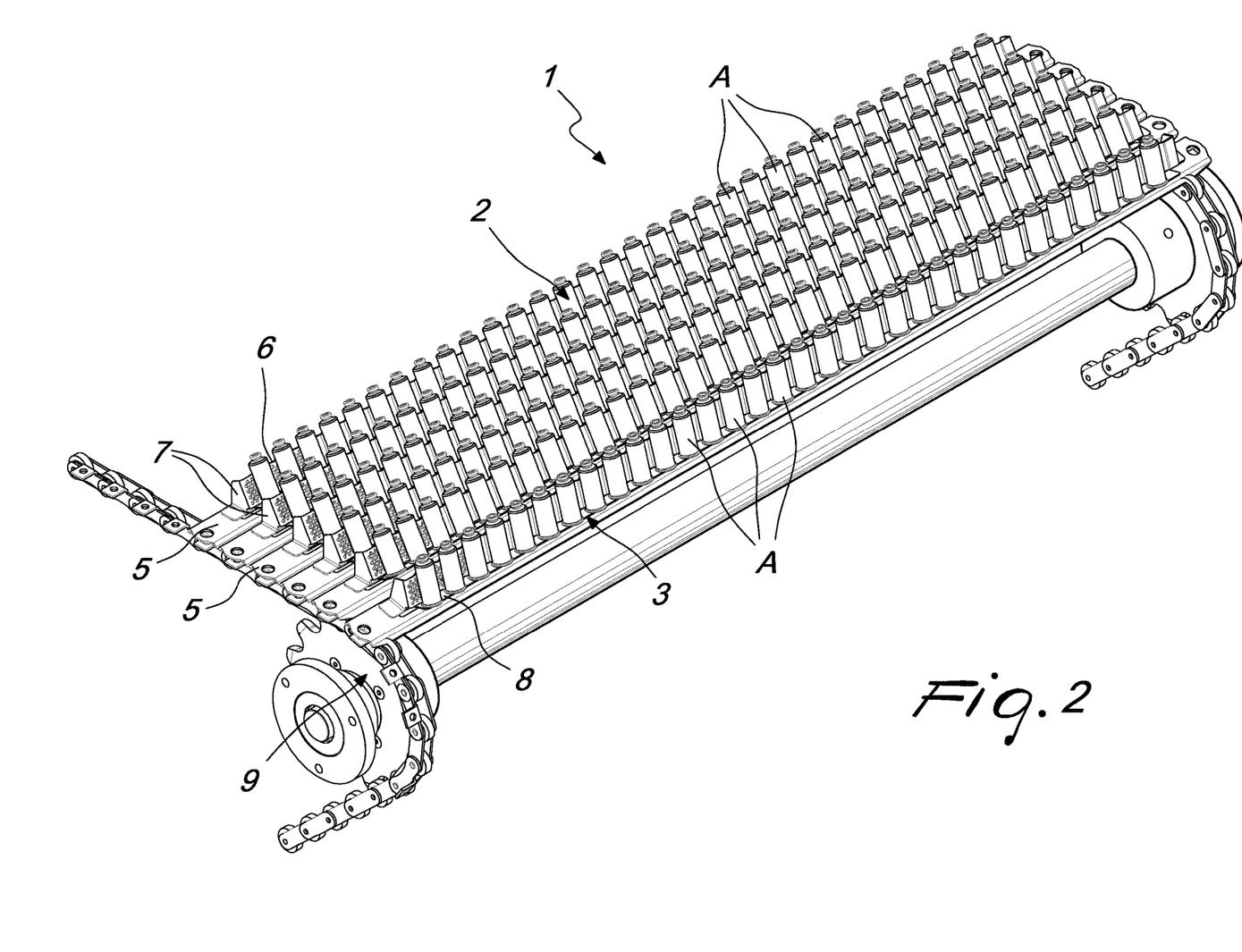
FIG. 2 is an enlarged-scale view of a detail of FIG. 1.
Figure 3:
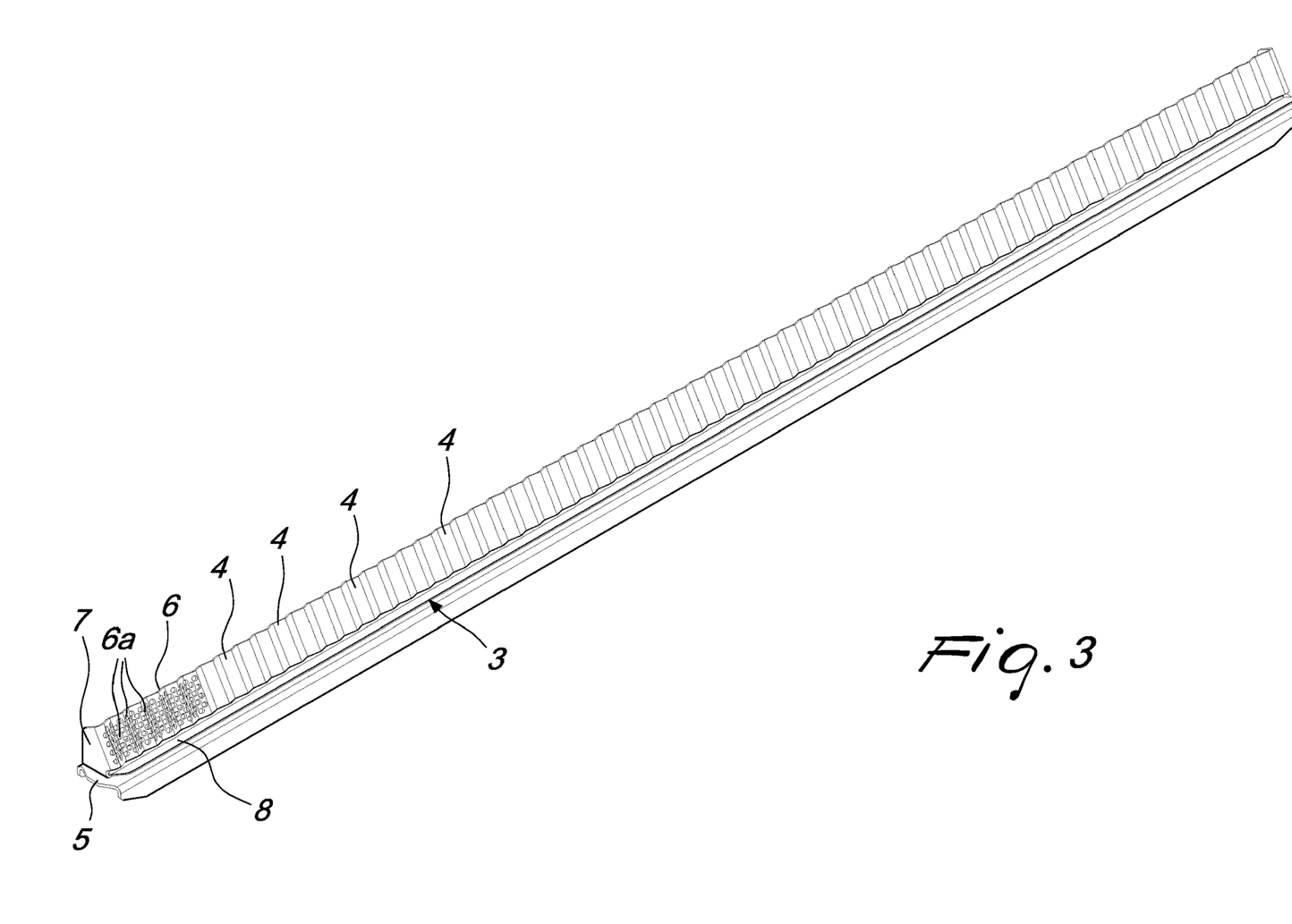
FIG. 3 is a perspective view of a supporting strip of the group of FIG. 1.
Figure 4:
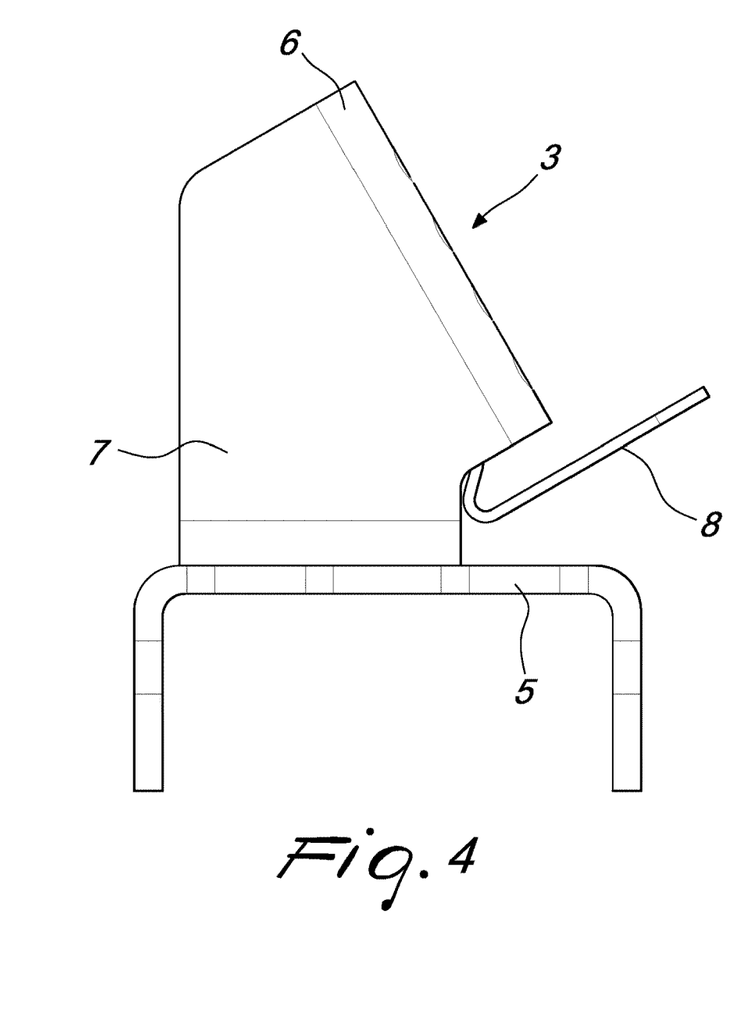
FIG. 4 is a side view of the strip of FIG. 3.
Figure 5:
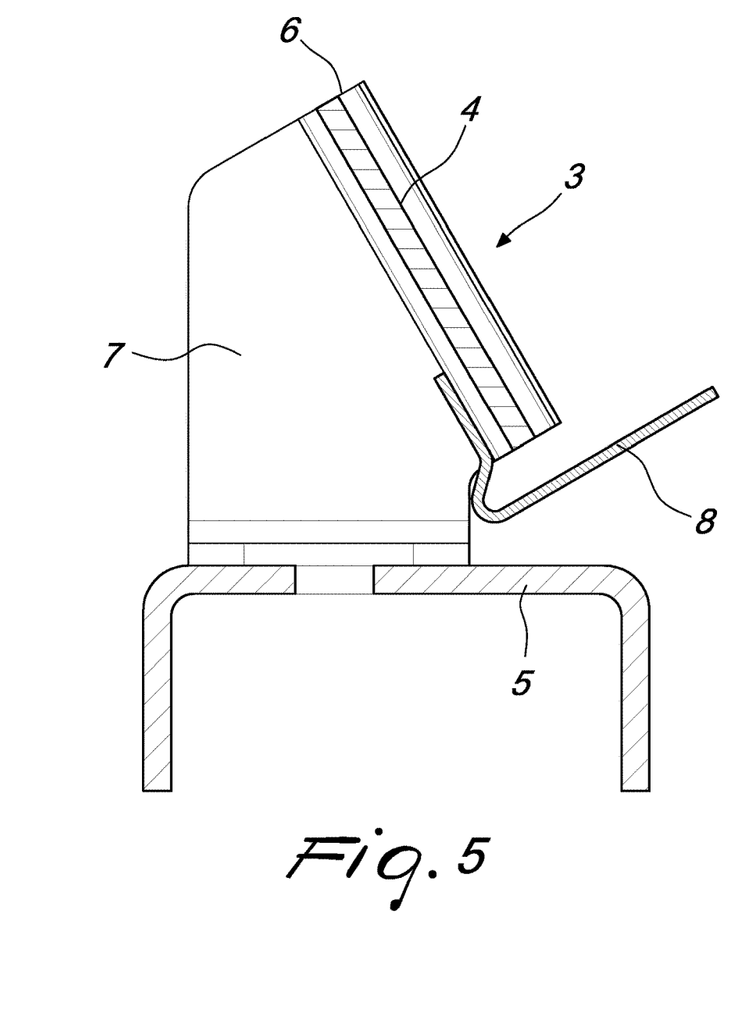
FIG. 5 is a sectional side view, taken along a transverse plane, of the strip of FIG. 3.

It is sufficient for the ends of each support element 3 to be associated with the driving element 9 (hypothetically a chain, as shown by way of nonlimiting example in FIGS. 1 and 2) in order to ensure that the support elements 3 can advance in mutually parallel conditions of mutual parallel arrangement and can slide inside, for example, a sterilization chamber.

The transport group 1 is therefore suitable to slide within a sterilization chamber, so that the containers A supported by the support elements 3 undergo a sterilization and/or depyrogenation treatment.

Figure 6:
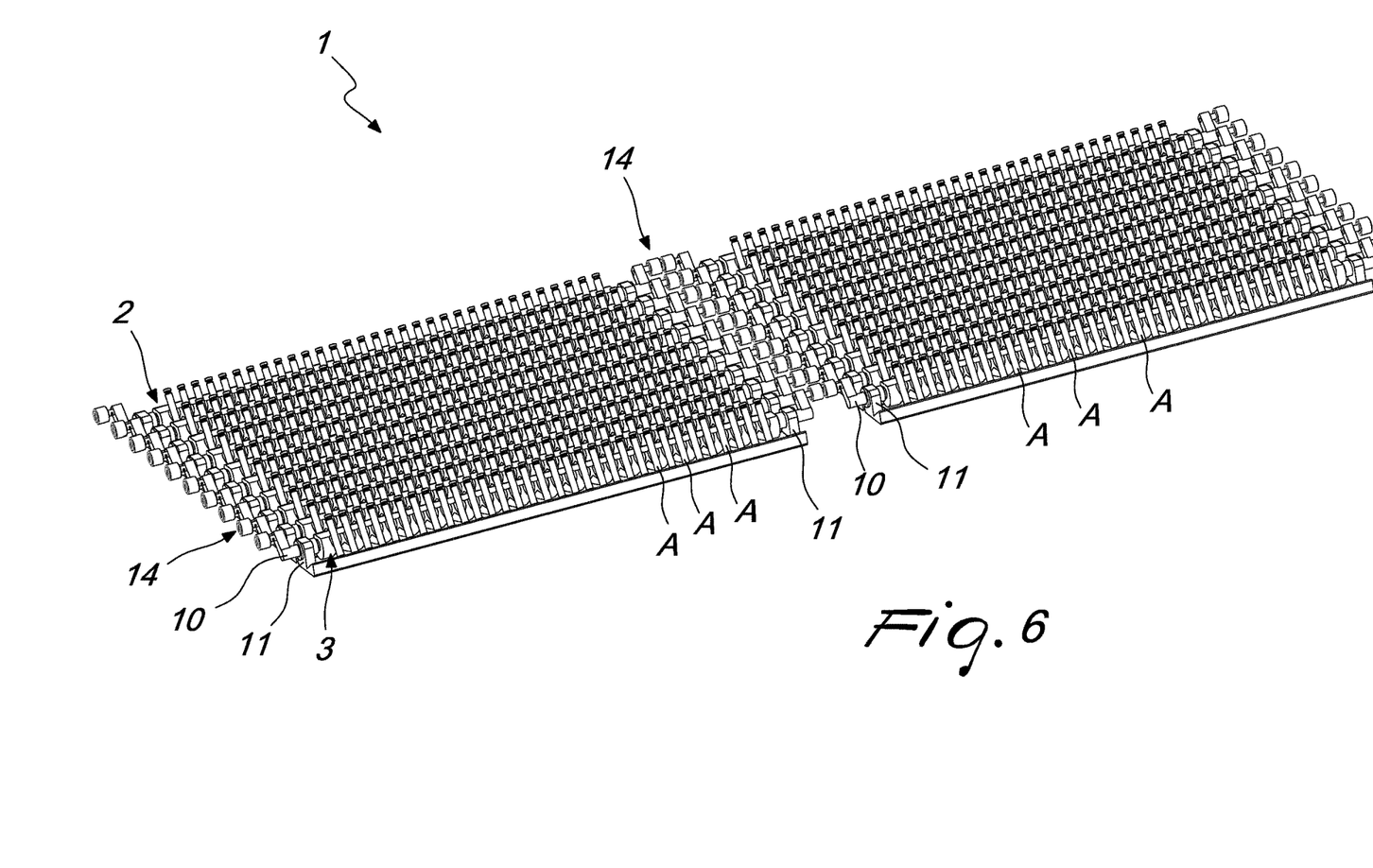
FIG. 6 is a perspective top view of a constructive variation of a transport group for container sterilization apparatuses according to the disclosure.
Figure 7:
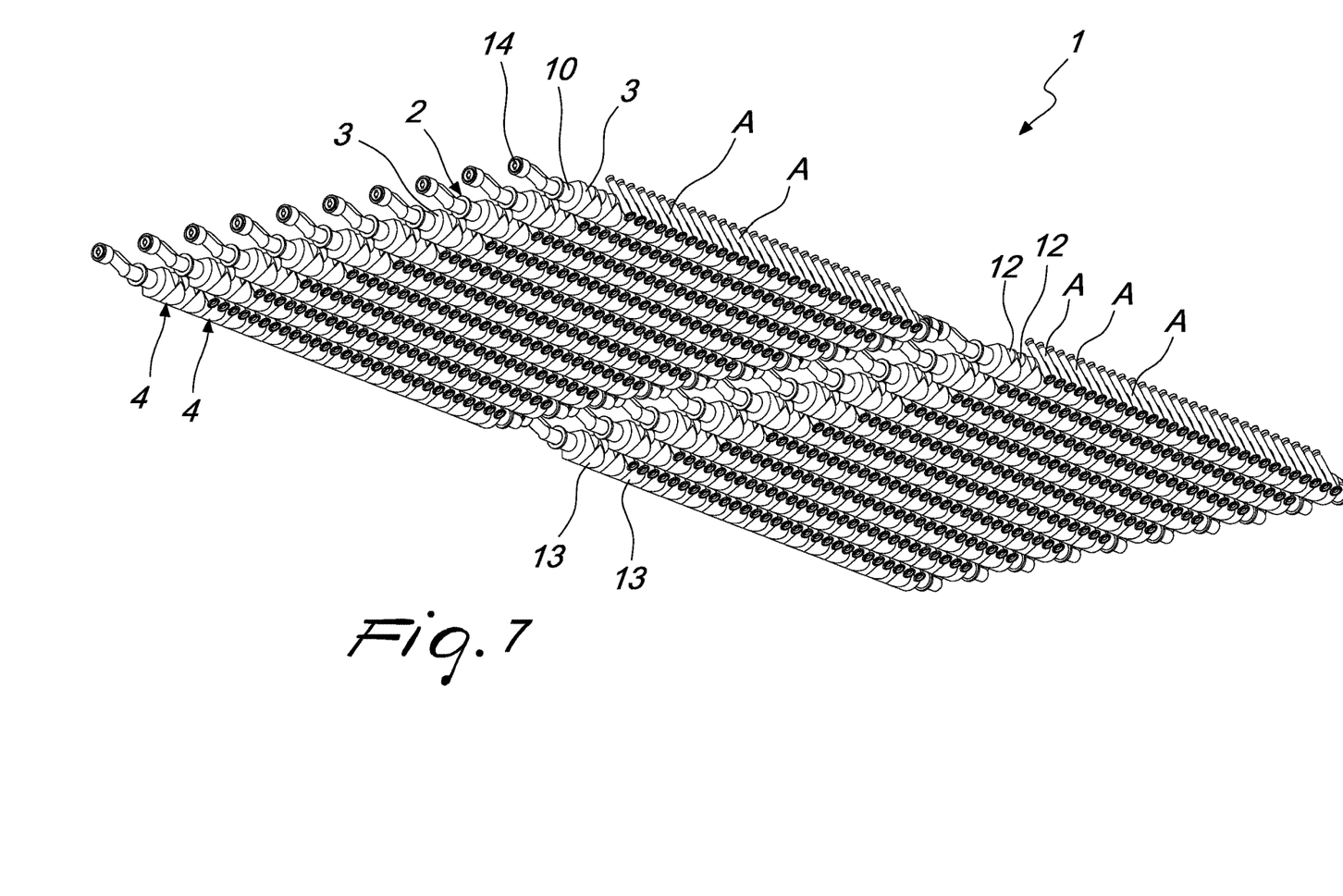
FIG. 7 is a perspective view, taken from below, of the constructive variation of FIG. 6.

According to an alternative constructive solution, shown in FIGS. 6 and 7, each support element 3 can advantageously comprise a bar 10, which has a shape that is selected preferably from prismatic, cylindrical, frusto-conical and the like.

The bars 10 can move by rotating about their own longitudinal axis.

The bars 10 are coupled rotatably, by means of hinges 11, to the conveyor belt 2.

Each bar 10 is provided with a peripheral surface on which notches are formed which define the shaped seats 4. Preferably, the notches have converging walls with a substantially V-shaped profile, such as to be able to accommodate containers of a different size within a predetermined range. The notches are aligned along at least one generating line.

Advantageously, each bar 10 comprises at least one plurality of first notches 12 and a plurality of second notches 13, which are arranged on respective and mutually different generating lines.

The first notches 12 are different from the second notches 13; in particular, the first notches 12 can differ from the second notches 13 in terms of size and/or shape.

For example, the first notches 12 have a depth (and therefore a width) that is smaller than that of the second notches 13: the first notches 12 are therefore suitable to house containers A that are smaller than the containers A that can be housed in the second notches 13. Obviously, due to their size difference, the first notches 12 are arranged on the bar 10 according to a spacing that is different from, in particular smaller than, the spacing along which the second notches 13 are arranged.

According to the constructive solution that has just been defined, the bars 10 aligned and coupled rotatably to the conveyor belt 2 are a plurality, all provided with first notches 12 and second notches 13, respectively having the same shape and dimensions, which are aligned and laterally adjacent along respective generating lines.

Each bar 10 comprises a respective orientation element 14 in order to rotate, as a consequence of a specific external action, and arrange in the operational position the notches (the first ones 12 or the second ones 13) that are suitable to house the containers A.

With respect to the preceding constructive solution, shown in FIGS. 1-5, the present alternative constructive solution has the additional advantage of being able to vary the inclination of the containers A by means of the orientation elements 14, which can vary in rotation the operational position of the notches 12, 13.

It is evident that small containers A can be housed equally in the first notches 12 or in the second notches 13, but due to the different spacing according to which the first and second notches 12 and 13 are arranged, it is advantageous, in order to maximize the number of conveyed containers A, to use the first notches 12 as long as this is allowed by the size of the containers A.

The orientation element 14 can be constituted by an arm that protrudes in a radial direction from the respective bar 10: the end of the arm comprises validly a probe, or a roller, which moves along a cam. All the bars 10 are provided with respective arms provided with corresponding probes and are mutually aligned. The path of the cam, on which the probes of all the bars 10 act, therefore determines the rotation of each bar 10 and the orientation of the provided notch 12 or 13.

The present disclosure extends its protection also to a sterilization apparatus for containers A which comprises a feed station, a sterilization station, a cooling station, and a group 1 for the transport of containers A as described above, which passes through the stations.

Advantageously, the present disclosure solves the problems described previously, proposing a transport group 1 for apparatuses for sterilizing containers A that is suitable to convey containers A of substantially any shape and size.

The shaped seats 4 formed in the group 1 according to the disclosure in fact can accommodate containers A of a shape and size that can vary within a relatively broad range.

In particular, the first constructive embodiment described, which comprises the shaped plate 6, comprises a plurality of contiguous shaped seats 4 within which it is possible to house (with a density that is inversely proportional to the diameter) containers of various shapes and sizes. For example, it is possible to accommodate relatively small containers (for example vials) mutually side by side, arranging one in each shaped seat 4 formed on each shaped plate 6; for relatively large containers (for example bottles) it is instead necessary to leave a certain number of empty shaped seats 4 (at least one) between adjacent containers.

In any case, advantageously, the bases of the containers A (be they vials, bottles, carpules, syringes, jars and the like) rest on the lower ledge 8.

In the case of the second embodiment described, which comprises the bars 10, it is instead possible to house small containers A by rotating the bars 10 (by means of the orientation element 14) so that the seats 12 are directed laterally in the operational position, or it is possible to house large containers A by rotating the bars 10 (by means of the orientation element 14) so that the seats 13 are directed laterally in the operational position.

Advantageously, therefore, the transport group 1 according to the disclosure allows to maximize the number of containers that are conveyed simultaneously as a function of their dimensions. It has in fact been shown that the surface density of containers A provided by the transport group 1 depends uniquely on the dimensions of the containers A.

In particular, by means of the group 1 according to the disclosure it is always possible to approximate the maximum surface density of containers A, arranging them so that they are at the minimum possible mutual distance while avoiding mutual contact.

The particular structural shape and the characteristics of the transport group 1 according to the disclosure ensure that no complex operations are required to change format.

In the provided embodiment of the shaped plate 6 no operation is necessary upon the change of format of the container A to be transported.

Conveniently, the transport group 1 according to the disclosure is easy to use.

Finally, validly, the transport group 1 according to the disclosure is relatively simple to provide in practice, bearing substantially modest costs: these characteristics make it an innovation of assured application.

By virtue of the particular shape of the transport group 1 according to the disclosure, it is appropriate to specify that the movement of the containers A (in particular their arrangement in the seats 4 of the element 3 and their respective pickup) can be performed positively by means of a handling robot (for example an anthropomorphic robot): this possibility is ensured by the fact that the containers A are simply rested in their respective seats 4 (they are not engaged, since the seat 4 does not form a housing that is shaped complementarily to the individual container A but it forms a region at which it can be simply rested stably).

The disclosure thus conceived is susceptible of numerous modifications and variations; all the details may further be replaced with other technically equivalent elements.

In the exemplary embodiments shown, individual characteristics, given in relation to specific examples, may actually be interchanged with other different characteristics that exist in other exemplary embodiments.

In practice, the materials used, as well as the dimensions, may be any according to the requirements and the state of the art.

The disclosures in Italian Patent Application No. 102016000022285 (UA2016001312) from which this application claims priority are incorporated herein by reference.

The invention claimed is:

1. A transport group for container sterilization apparatuses, the transport group comprising:
   a conveyor belt, which defines an operational plane and advances along an advancement direction; and
   a plurality of support elements, mutually separated, and integral and movable with the conveyor belt, each support element having longitudinal development, transverse to the advancement direction and lying along a direction parallel to the operational plane,
   wherein each support element defines a plurality of shaped seats arranged along said longitudinal development, each shaped seat being adapted to temporarily house a respective container, said shaped seats having a substantially V-shaped cross section, such as to house containers of different size within a predetermined range, said shaped seats having a longitudinal development inclined with respect to the advancement direction, so that the containers, temporarily housed in respective said shaped seats, result inclined with respect to said advancement direction when the containers are moved by said conveyor belt.

2. The transport group according to claim 1, wherein said shaped seats comprise at least two contact points for contacting the respective containers.

3. The transport group according to claim 1, wherein each said support element is coupled to at least one driving element.

4. The transport group according to claim 1, wherein each said support element comprises a base laminar element, integral with said conveyor belt, and a shaped plate, protruding and substantially inclined with respect to said base laminar element; said shaped plate comprising a succession of mutually inclined consecutive tracts which realize a continuous succession of concavities, defining said shaped seats, and convexities.

5. The transport group according to claim 4, wherein between said base laminar element and said shaped plate are interposed support ribs substantially orthogonal to said base laminar element.

6. The transport group according to claim 1, wherein each said support element comprises a bar with a shape selected between prismatic, cylindrical, and frusto-conical, rotatably bound, by means of hinges, to said conveyor belt, along a peripheral surface of each said bar being defined notches which define said shaped seats.

7. The transport group according to claim 6, wherein each said bar comprises a plurality of said first notches and a plurality of said second notches, arranged along respective generating lines, mutually different, said first notches being different from said second notches.

8. The transport group according to claim 7, wherein each said bar comprises an orientation element, in order to rotate, as a result of a specific external action, and arrange in operative position said notches suitable for housing the containers.

9. A sterilization apparatus for containers comprising a feeding station for feeding said containers, a sterilization station for sterilizing said containers, a cooling station for cooling said containers and a transport group of said containers according to claim 2, said transport group passing through said feeding station, said sterilization station and said cooling station.

10. The transport group according to claim 1, wherein said shaped seats comprise at least two contact lines for contacting the respective containers.

11. The transport group according to claim 1, wherein each said support element is coupled to at least one driving element selected from a chain, a belt, and a cable, operatively associated with a drive unit.

* * * * *